(12) United States Patent
Peilstöcker et al.

(10) Patent No.: US 6,903,239 B2
(45) Date of Patent: Jun. 7, 2005

(54) FLUORINATED BENZALDEHYDES

(75) Inventors: Karen Peilstöcker, Köln (DE); Albrecht Marhold, Leverkusen (DE)

(73) Assignee: Bayer Chemical Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/718,758

(22) Filed: Nov. 21, 2003

(65) Prior Publication Data

US 2004/0133043 A1 Jul. 8, 2004

(30) Foreign Application Priority Data

Dec. 9, 2002 (DE) .......................................... 102 57 357

(51) Int. Cl.[7] .......................... C07C 45/37; C07C 39/24; C07C 211/00; A61K 31/11
(52) U.S. Cl. ....................... 568/436; 568/442; 568/775; 568/782; 568/796; 564/336; 514/699; 514/731
(58) Field of Search ................................ 568/436, 442, 568/775, 782, 796; 564/336; 514/699, 731

(56) References Cited

U.S. PATENT DOCUMENTS

| | | | |
|---|---|---|---|
| 4,388,472 A | 6/1983 | Cartwright et al. ............ | 560/21 |
| 4,588,844 A | 5/1986 | Kysela et al. .................. | 568/41 |
| 5,294,744 A | 3/1994 | Godek et al. ................. | 568/442 |
| 5,955,495 A | 9/1999 | Bös et al. .................... | 514/469 |
| 2004/0019113 A1 | 1/2004 | Jozeflak et al. ............. | 514/602 |

FOREIGN PATENT DOCUMENTS

| | | |
|---|---|---|
| DE | 3836161 | 4/1990 |
| EP | 370219 | 10/1989 |
| WO | 01/19780 | 3/2001 |

OTHER PUBLICATIONS

Andriamanantena, R. et al: "Antimalarial activities of new hydroxy(trifluoromethyl) benzylamine salts" European Journal of Medicinal Chemistry, 26(5), 535–7 CODEN: EJMCA5; ISSN: 0223–5234, 1991, XP002273154 *das ganze Dokument*.

Bream, R.N. et al: "Synthesis of the beta2 agonist (R)–Salmeterol using a sequence of supported reagents and scavenging agents" Organic Letters., Bd. 4, Nr. 22, 2002, Seiten 3793–3796. XP002273155 USACS, Washington, D.C. *Tabelle I, Verbindung 3*.

Nelson P. H. et al: "Structure–activity relationships for inhibition of inosine monophosphate dehydrogenase by nuclear variants of mycophenolic acid" Journal of Medicinal Chemistry., Bd. 39, Nr. 21, 1996, Seiten 4181–4196, XP002273156 USAmerican Chemical Society. Washington. *Seite 4190, Verbindung 32a; Seite 4192 und 4193, Zwischenprodukte für die Herstellung von (3j), (3k) und (3m) *.

Becker B. C. et al: "Stereochemistry of diphenyl. XXIV. Preparation and properties of 2,2'–difluoro–3,3'–dicarboxy–6,6'–dimethoxydiphenyl" Journal of the American Chemical Society., Bd. 54, Nr. 7, 1932, Seiten 2973–2982, XP002273157 USAmerican Chemical Society, Washington, DC. *Seite 2975 und 2982, Verbindung der Formel XIV *.

Fukuhara T. et al: "Facile preparation of aromatic fluorides by the fluorodediazoniation of Aromatic diazonium tetrafluoroborates usisng HF–pyridine solution" Chemistry Letters., Nr. 6, 1994, Seiten 1011–1012, XP002273158 JPChemical Society of Japan. Tokyo. *Tabelle I, vorletzte Verbindung*.

Lock G.: "Über die Abspaltung der Aldehydgrappe als Ameisensäure aus aromatischen Aldehyden, IV: Mitteil.: 2–Chlor–6–fluor– und 2,6–Difluorbenzaldehyd." Chemische Berichte., Bd. 69, Nr. 10, 1936, Seiten 2253–2258, XP002273159 Deverlag Chemie GmbH. Weinheim. *Seire 2256, letze Absatz*.

Allen F. L. et al.: "Heterocyclic fluorine compounds—III Monoflurorxanthones" Tetrahedron., Bd. 6, Nr. 4, 1959, Seiten 315–318, XP002273160 NLElsevier Science Publishers, Amsterdam. *Seite 316, "experimental"*.

Fukuhara T. et al: "The preparation of p–fluorophenols from p–aminophenols: diazotization and fluorodediazoniation in Pyridine–HF" Journal of Fluorine Chemistry., Bd. 51, Nr. 2, 1991, Seiten 299–304, XP002273161 CHElsevier Sequoia. Lausanne. *Tabelle 1*.

Sharma, G.V.M. et al: "Synthesis of 5–fluorosalicyclic acid" Synthetic Communications, 30(3), 397–405 CODEN: SYNCAV; ISSN: 0039–7911, 2000, XP000802828 *Verbindung 3*.

Brycki B. et al.: Preparation and NMR characterisation of hydrogen bonding in 2– and 2,6–bis(N, N–diethylaminomethyl)–4R–phenols: Journal of Molecular Structure,. Bd. 246, Nr. 1, 1991, Seiten 61–71, XP000802828 NLElsevier, Amsterdam. *Seite 62*.

Suzuki et al., Chem. Pharm. Bull. 1963, 31(5), pp. 1751–1753, "Formylation of Phenols with Electron–withdrawing Groups in Strong Acids. Synthesis of Substituted Salicylaldehydes".

*Primary Examiner*—Johann Richter
*Assistant Examiner*—Sikarl A. Witherspoon
(74) *Attorney, Agent, or Firm*—Diderico van Eyl

(57) ABSTRACT

The present invention relates to fluorinated benzaldehydes, to a process for preparing them and also to the use of the fluorinated benzaldehydes for preparing active ingredients, especially in medicaments and agrochemicals.

21 Claims, No Drawings

FLUORINATED BENZALDEHYDES

BACKGROUND OF THE INVENTION

1. Field of the Invention

The present invention relates to fluorinated benzaldehydes, to a process for preparing them and also to the use of the fluorinated benzaldehydes for preparing active ingredients, especially in medicaments and agrochemicals.

2. Brief Description of the Prior Art

Fluorinated benzaldehydes, for example fluorinated 2-hydroxy- and 2-alkoxybenzaldehydes, are valuable starting materials for the preparation of active ingredients in medicaments and agrochemicals. Their the fluorine or fluorinated substituents increase the lipophilicity and therefore the ability of the entire active ingredient molecule to pass through membranes. For example, compounds such as 5-fluoro-2-hydroxybenzaldehyde are suitable as the starting material for preparing medicaments which are used for treating cardiovascular diseases (see also WO-A 01/19780, p.81).

Of particular concern here are the methods of preparing fluorinated benzaldehydes and the attendant disadvantages are described as follows. Illustratively, 5-fluoro-2-hydroxybenzaldehyde can be prepared, for example, by formylating 4-fluorophenol (Suzuki et al., Chem. Pharm. Bull. 1963, 31(5), 1751–1753). However, the yields at less than 20% of theory are not acceptable.

There is therefore a need to provide fluorinated 2-hydroxy-3-methylbenzaldehydes and an efficient process for the preparation thereof.

SUMMARY OF THE INVENTION

A process has now been found for preparing compounds of the formula (I)

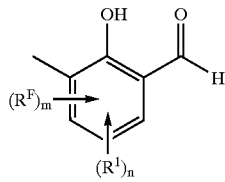

(I)

where
R$^1$ is in each case independently C$_1$–C$_{12}$-alkyl, chlorine or bromine or a radical of the formulae (IIa) or (IIb)

A-B-D-E (IIa)

A-E (IIb)

where, each independently,
A is absent or is a C$_1$–C$_8$-alkylene radical and
B is absent or is oxygen, sulphur or NR$^2$
where R$^2$ is hydrogen or C$_1$–C$_8$-alkyl and
D is a carbonyl group and
E is C$_1$–C$_8$-alkyl, C$_1$–C$_8$-alkoxy, NH(C$_1$–C$_8$-alkyl) or N(C$_1$–C$_8$-alkyl)$_2$ or is a cyclic amino radical having 4 to 12 carbon atoms and
n is an integer of 0 to 3-m and
R$^F$ is fluorine, C$_1$–C$_{12}$-fluoroalkyl, —O(C$_1$–C$_{12}$-fluoroalkyl) or —S(C$_1$–C$_{12}$-fluoroalkyl) and
m is an integer of 1 to 3, which is characterized in that compounds of the formula (II)

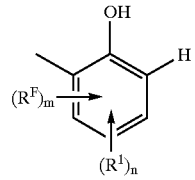

(II)

where
R$^1$ and R$^F$, and also n and m, are as defined above are converted
in the presence of urotropin and
in the presence of acid
to compounds of the formula (I).

Within the scope of the invention, all of the radical definitions, parameters and illustrations hereinabove and cited hereinbelow, specified in general or within preferred ranges i.e. the particular areas and areas of preference, may be combined as desired.

DETAILED DESCRIPTION OF THE INVENTION

Alkyl, alkylene, alkoxy and alkenyl are in each case independently a straight-chain, cyclic, branched or unbranched alkyl, alkylene, alkoxy and alkenyl radical respectively. The same applies to the nonaromatic moiety of an arylalkyl radical.

C$_1$–C$_4$-Alkyl is, for example, methyl, ethyl, n-propyl, isopropyl, n-butyl, sec-butyl and tert-butyl, C$_1$–C$_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, and C$_1$–C$_{12}$-alkyl is still further additionally, for example, adamantyl, n-nonyl, n-decyl and n-dodecyl.

C$_1$–C$_8$-Alkoxy is, for example, methoxy, ethoxy, n-propoxy, isopropoxy, n-butoxy, sec-butoxy and tert-butoxy, n-pentoxy, 1-methylbutoxy, 2-methylbutoxy, 3-methylbutoxy, neopentoxy, 1-ethylpropoxy, cyclohexoxy, cyclopentoxy, n-hexoxy and n-octoxy.

Fluoroalkyl is in each case independently a straight-chain, cyclic, branched or unbranched alkyl radical which is substituted by at least one fluorine atom and optionally further by chlorine atoms and/or bromine atoms.

C$_1$–C$_{12}$-Polyfluoroalkyl is, for example, trifluoromethyl, chlorofluoromethyl, difluoromethyl, difluorochloromethyl, 1,1,2,2-tetrafluoro-1-ethyl, 2-chloro-2,1,1-trifluoro-1-ethyl, 2,2,2-trifluoroethyl, pentafluoroethyl, 1,1-dichloro-2,2,2-trifluoroethyl, heptafluoroisopropyl, n-nonafluorobutyl, perfluorocyclopentyl, perfluorocyclohexyl and perfluorododecyl.

The preferred substitution patterns for compounds of the formulae (I) and (II) are defined hereinbelow:

R$^1$ is preferably in each case independently C$_1$–C$_4$-alkyl or chlorine, more preferably methyl.

n is preferably 0 or 1, more preferably 0.

$R^F$ is preferably fluorine, $C_1$–$C_4$-fluoroalkyl, —O($C_1$–$C_4$-fluoroalkyl) or —S($C_1$–$C_4$-fluoroalkyl), more preferably trifluoromethyl, trifluoromethylthio, trifluoromethoxy, chlorofluoromethyl, chlorofluoromethylthio, chlorofluoromethoxy, difluoromethoxy, difluoromethyl, difluoromethylthio, difluoromethoxy, difluorochloromethyl, difluorochloromethylthio, difluorochloromethoxy, 1,1,2,2-tetrafluoro-1-ethyl, 1,1,2,2-tetrafluoro-1-ethylthio, 1,1,2,2-tetrafluoro-1-ethoxy, 2-chloro-2,1,1-trifluoro-1-ethyl, 2-chloro-2,1,1-trifluoro-1-ethylthio, 2-chloro-2,1,1-trifluoro-1-ethoxy, 2,2,2-trifluoroethyl, 2,2,2-trifluoroethylthio, 2,2,2-trifluoroethoxy, pentafluoroethyl, pentafluoroethylthio, pentafluoroethoxy, 1,1-dichloro-2,2,2-trifluoroethyl, 1,1-dichloro-2,2,2-tri-fluoroethylthio, 1,1-dichloro-2,2,2-trifluoroethoxy, heptafluoroisopropyl, n-nonafluorobutyl, perfluorocyclopentyl, perfluorocyclohexyl and perfluorododecyl.

m, in the case that all $R^F$ are fluorine, is an integer of 1 to 3, otherwise one or two, preferably one.

The compounds of the formula (II) are converted in the presence of urotropin and in the presence of acid to compounds of the formula (I).

The molar ratio of urotropin to compounds of the formula (II) may be, for example, 1:1 to 10:1, preferably 1:1 to 5: and more preferably 1.5:1 to 2.5:1.

The molar ratio of acid to compounds of the formula (II) may be, for example, 1:1 to 100:1, preferably 3:1 to 10:1.

The acid used is preferably one which, based on an aqueous reference system and 25° C., has a pKa value of 3 or less.

Particularly preferred acids are perfluoroalkylcarboxylic acids, ortho-phosphoric acid and polyphosphoric acids, organic sulphonic acids, hydrochloric, hydrobromic or hydriodic acid optionally dissolved in acetic acid, hydrogen sulphates and sulphuric acid, and greater preference is given to hydrobromic acid in acetic acid, polyphorphoric acids, methanesulphonic acid and trifluoroacetic acid, and still greater preference to trifluoroacetic acid.

Optionally, organic solvents may also be added to the reaction mixture, as long as they are substantially inert under the specified reaction conditions.

Preference is given to carrying out the reaction in the acid used.

The reaction temperature may be, for example, 0° C. to 150° C., preferably 30 to 150° C. and more preferably 70 to 110° C.

The reaction pressure may be, for example, 0.5 to 100 bar, although preference is given to ambient pressure.

The procedure for converting the compounds of the formula (II) is, for example, that the compounds of the formula (II) and the acid are initially charged and the urotropin is subsequently added.

The compounds of the formula (I) can be worked up in a manner known per se by extraction and subsequent distillation or, in the case of compounds of the formula (I) which are solid at 30° C., by recrystallization.

The compounds of the formula (I) are likewise encompassed by the invention. The statements made above apply similarly to the areas of preference.

Particularly preferred individual compounds of the formula (I) include:

5-fluoro-2-hydroxy-3-methylbenzaldehyde, 5,6-difluoro-2-hydroxy-3-methylbenzaldehyde and 2-hydroxy-3-methyl-5-(trifluoromethoxy)benzaldehyde.

Preference is given, for example, to preparing compounds of the formula (I) with compounds of formula (II) obtained by converting compounds of the formula (III)

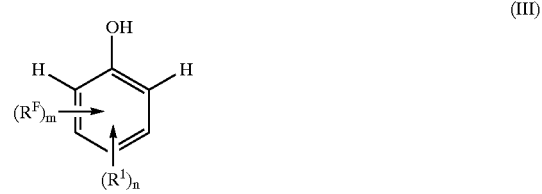

(III)

where $R^1$, $R^F$ and m each have the definition and areas of preference specified above and n is an integer between 0 and 3-m, a) in the presence of formaldehyde and
in the presence of secondary amines of the formula (IV)

$$HNR^3R^4 \qquad (IV)$$

where $R^3$ and $R^4$ are each independently $C_1$–$C_8$-alkyl or $NR^3R^4$ as a whole is a cyclic amino radical having a total of 4 to 12 carbon atoms, to compounds of the formula (V)

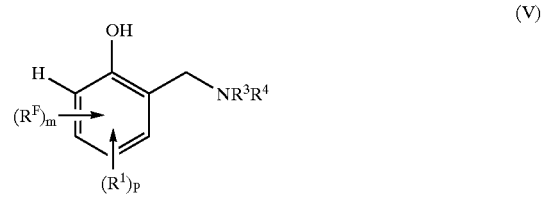

(V)

where $R^1$, $R^3$, $R^4$ and $R^F$, and also n and m, each have the definition and areas of preference specified above, and b) reducing the compounds of the formula (V) to compounds of the formula (II).

As important intermediates, the compounds of the formula (II) are likewise encompassed by the invention, with the exception of 2-methyl-4-fluorophenol.

Particularly preferred individual compounds of the formula (II) include: 4-fluoro-2-methylphenol, 4,5-difluoro-2-methylphenol and 2- methyl-4-(trifluoromethoxy)phenol.

The statements made above apply similarly to the areas of preference.

As important intermediates, the compounds of the formula (V) are additionally encompassed by the invention, with the exception of 5-fluoro-2-hydroxy-N,N-dimethylbenzylamine. Particularly preferred individual compounds of the formula (V) include: 4,5-difluoro-2-hydroxy-N,N-dimethylbenzylamine, 2-hydroxy-5-(trifluoromethoxy)-N,N-dimethylbenzylamine, 6-hydroxy-2,3,4-trifluoro-N,N-dimethylbenzylamine and 2-hydroxy-4-(trifluoromethyl)-N,N-dimethylbenzylamine. The statements made above apply similarly to the areas of preference.

In step a), the compounds of the formula (III) are converted in the presence of formaldehyde and in the presence of secondary amines of the formula (IV) to compounds of the formula (V).

The molar ratio of formaldehyde to compounds of the formula (III) may, for example, be 0.8 to 10, preferably 1.0 to 10 and more preferably 1.2 to 3.6.

The molar ratio of secondary amines of the formula (IV) to compounds of the formula (III) may be, for example, 0.8 to 10, preferably 1.0 to 10 and more preferably 1.05 to 3.15.

Formaldehyde may be used, for example, as paraformaldehyde and/or in the form of an aqueous solution, preferably in the form of a 32 to 40% by weight solution.

The secondary amines of the formula (IV) can be used, for example, without solvents or, where possible, in the form of aqueous solutions. Particular preference is given to using dimethylamine in the form of an aqueous solution.

The reaction temperature may be, for example, −40° C. to 120° C., preferably −10 to 40° C. and more preferably −5 to 10° C.

The reaction pressure may be, for example, 0.5 to 100 bar, although preference is given to ambient pressure.

The reaction time may be 10 min to 72 hours, preferably 3 hours to 24 hours.

An example of a possible procedure for the reaction is to initially charge the compounds of the formula (III) and the secondary amines of the formula (IV), and subsequently to add the formaldehyde.

The compounds of the formula (V) can be worked up in a manner known per se by extraction and subsequent distillation or, in the case of compounds of the formula (V) which are solid at 30° C., by recrystallization.

The reduction according to step b) may advantageously be carried out in the presence of hydrogen and hydrogenation catalyst.

Preferred hydrogenation catalysts are, for example, metals or metal compounds such as salts or complexes of nickel, palladium, platinum, cobalt, rhodium, iridium and ruthenium, although preference is given to metals such as nickel or palladium. Preference is given to using metals in finely divided form, for example as Raney metal or applied to a support material.

Particular preference is given to carrying out the reduction with hydrogen and Raney nickel and/or palladium on carbon.

The reduction may, for example, be carried out at a reaction temperature of 20° C. to 200° C., preferably 50 to 180° C. and more preferably 80 to 150° C.

The partial hydrogen pressure in the reduction may be, for example, 0.1 to 180 bar, preferably 10 to 150 bar and more preferably 40 to 120 bar.

Optionally and with preference, the reduction may be carried out in the presence of solvent, as long as it is substantially inert under the selected reaction conditions.

Suitable solvents are, for example, aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl or diethyl ether; alcohols, for example methanol, ethanol and isopropanol, carboxylic acids, for example acetic acid, or mixtures of solvents.

The reaction time in the reduction may be 10 min to 200 hours, preferably 5 to 100 hours.

In a particularly preferred embodiment, the reduction is carried out in the presence of palladium on activated carbon and in the presence of acetic acid at a partial hydrogen pressure of 40 to 120 bar.

The compounds of the formulae (I) and (II) obtainable according to the invention are suitable in particular in a process for preparing active ingredients, for example active ingredients for medicaments. Preferred active ingredients for medicaments are those which are used for treating cardiovascular diseases, such as described in WO-A 01/19780.

A substantial advantage of the invention is that the compounds of the formulae (I) and (II) can be prepared in a simple manner from readily available reactants. Moreover, the compounds of the formulae (I) and (II) according to the invention constitute valuable starting materials for the preparation of active ingredients, especially for medicaments.

The invention is further described by the following illustrative but non-limiting examples.

EXAMPLES

Example 1

Preparation of 5-fluoro-2-hydroxy-3-methylbenzaldehyde 84 g of 4-fluoro-2-methylphenol are dissolved in 512 ml of trifluoroacetic acid and admixed with 181 g of hexamethylenetetramine in portions. On completion of addition, the reaction solution is heated to 100° C. for 5 hours. After cooling, first 80 ml of 50% sulphuric acid and then 480 ml of water are added dropwise, then the solution is stirred further at room temperature for 3 hours. The reaction solution is extracted three times with dichloromethane. The combined extracts are washed once with water and dried, and the solvent is distilled off under reduced pressure. The residue is extracted repeatedly with n-hexane, the extracts are combined and the solvent is distilled off under reduced pressure. The crude product is subsequently fractionally distilled. 25 g (25% of theory) of a bright yellow solid are obtained having a melting point of 49–52° C. and a boiling point of 70–72° C. at 7 mbar.

The $^1$H NMR spectrum contained the following characteristic absorptions (CDCl$_3$, δ/ppm): 1.08 (s,1H, OH); 9.83 (s, 1H, CHO); 7.14, 7.07 (2×dd, 2H, H-4, H-6); 2.28 (s, 3H, CH$_3$).

Example 2

Preparation of 5,6-difluoro-2-hydroxy-3-methylbenzaldehyde 30 g of 4,5-difluoro-2-methylphenol are dissolved in 180 ml of trifluoroacetic acid and admixed with 57.2 g of hexamethylenetetramine in portions. On completion of addition, the reaction solution is heated to 97–100° C. for 4 hours. After cooling, first 60 ml of 50% sulphuric acid and then 300 ml of water are added dropwise, then the solution is stirred further at room temperature for 2 hours. The reaction solution is extracted three times with methyl tert-butyl ether. The combined extracts are washed once with water and dried, and the solvent is distilled off under reduced pressure. The residue is extracted repeatedly with n-hexane, the extracts are combined and the solvent is distilled off under reduced pressure. 12.5 g (33% of theory) of a bright yellow solid are obtained having a melting point of 53–56° C.

The $^1$H NMR spectrum contained the following characteristic absorptions (CDCl$_3$, δ/ppm): 11.39 (bs, 1H, OH); 10.24 (s, 1H, CHO); 7.23 (m, 1H, H-4); 2.22 (s, 3H, CH$_3$).

The following spectrum was obtained by means of GC-MS (EI, 70 eV, I/%): 172 (100, M$^+$).

Example 3

Preparation of 2-hydroxy-3-methyl-5-(trifluoromethoxy)benzaldehyde 100 g of 2-methyl-4-(trifluoromethoxy)phenyl are dissolved in 600 ml of tri-fluoroacetic acid and admixed with 144 g of hexamethylenetetramine in portions. On completion of addition, the reaction solution is heated to 100° C. for 16 hours. After cooling, first 200 ml of 50% sulphuric acid and then 700 ml of water are added dropwise, then the solution is stirred further at room temperature for 3 hours. Extraction is effected three times using methyl tert-butyl ether and the combined organic phases are washed once with water and dried, and the solvent is distilled off under reduced pressure. The residue is extracted repeatedly with n-hexane, the extracts are combined and the solvent is distilled off under reduced pressure. The product can be further purified by distillation. 40 g (34% of theory) of a pale yellow liquid are obtained having a boiling point of 65–67° C. at 4 mbar.

The $^1$H NMR spectrum contained the following characteristic absorptions (DMSO-d6, δ/ppm): 11.03 (bs, 1H, OH); 10.12 (s, 1H, CHO); 7.59, 7.48 (2×m, 2H, H-4,H-6); 2.26 (s, 3H, CH$_3$).

The following spectrum was obtained by GC-MS (EI, 70 eV, I/%): 220 (100, M$^+$).

Example 4

Preparation of 4,5-difluoro-2-hydroxy-N,N-dimethylbenzylamine 400 g of 3,4-difluorophenol are initially charged in 408 ml of 40% aqueous dimethylamine solution and cooled to 0° C. At 0–5° C., 276 ml of 37% aqueous formaldehyde solution are added dropwise within 60 min. The mixture is kept at 5–10° C. for 2 hours and subsequently stirred at room temperature for 20 hours. The mixture is admixed with 600 ml of water. The organic phase is removed, the aqueous phase is extracted twice with dichloromethane, the combined organic phases are dried and the solvent is distilled off under reduced pressure. The crude product is subsequently fractionally distilled under reduced pressure. 395 g (65% of theory) of a colourless liquid having a boiling point of 93° C. at 16 mbar are obtained.

The $^1$H NMR spectrum contained the following characteristic absorptions (CDCl$_3$, δ/ppm): 11.32 (s, 1H, OH); 7.77, 7.60 (2 m, 2H, H-3, H-6); 3.57 (s, 2H, CH$_2$); 2.32 (s, 6H, N(CH$_3$)$_2$).

The following spectrum was obtained by GC-MS (EI, 70 eV, I/%): 187 (100, M$^+$); 143 (36, (M-N(CH$_3$)$_2$)$^+$).

Example 5

Preparation of 2-hydroxy-5-(trifluoromethoxy)-N,N-dimethylbenzylamine 130 g of 4-trifluoromethoxyphenol are initially charged in 97 ml of 40% aqueous dimethylamine solution and cooled to 3° C. At 0–5° C., 66 ml of 37% aqueous formaldehyde solution are added dropwise within 45 min. The mixture is kept at 5–10° C. for a further 2 hours and is subsequently stirred at room temperature for 19 hours. It is cooled again to 0° C., 4.9 ml of 40% aqueous dimethylamine solution are added and 3.3 ml of 37% aqueous formaldehyde solution are subsequently added dropwise. The mixture is stirred at room temperature for a further 3 hours. The mixture is admixed with 100 ml of water. The organic phase is removed, the aqueous phase is extracted twice with dichloromethane, the combined organic phases are dried and the solvent is distilled off under reduced pressure. The crude product is subsequently fractionally distilled under reduced pressure. 118 g (69% of theory) of a light yellow liquid having a boiling point of 110–112° C. at 18 mbar were obtained.

The $^1$H NMR spectrum contained the following characteristic absorptions (CDCl$_3$, δ/ppm): 11.08 (bs, 1H, OH); 7.03 (dd, 1H, J$_{H4-H3}$=8.9 Hz, J$_{H-4-H6}$=2.4 Hz, H-4); 6.84 (d, 1H, J$_{H-6, H-4}$=2.3 Hz, H-6); 6.80 (d, 1H, J$_{H3-H4}$=8.8 Hz, H-3); 3.62 (s, 2H, CH$_2$); 2.32 (s, 3H, CH$_3$).

The following spectrum was obtained by means of GC-MS (EI, 70 eV, I/%): 235 (100, M$^+$); 191 (19, (M-N(CH$_3$)$_2$)$^+$).

Example 6

Preparation of 6-hydroxy-2,3,4-trifluoro-N,N-dimethylbenzylamine 400 g of 3,4,5-trifluorophenol are initially charged in 359 ml of 40% aqueous dimethylamine solution and cooled to 0° C. At 0–5° C., 243 ml of 37% aqueous formaldehyde solution are added dropwise within 90 min. Subsequently, the mixture is stirred at room temperature for 20 hours. The mixture is admixed with 600 ml of water and 500 ml of dichloromethane. The organic phase is removed, the aqueous phase is extracted once with dichloromethane, the combined organic phases are dried and the solvent is distilled off under reduced pressure. The crude product is taken up in 500 ml of water and adjusted to pH 1–2 with cooling in an ice bath using dilute hydrochloric acid. The acidic solution is extracted once with dichloromethane and subsequently adjusted to pH 8–9 with cooling in an ice bath using dilute sodium hydroxide solution. The alkaline reaction solution is extracted three times with dichloromethane, the combined organic phases are washed once with water and dried, and the solvent is removed under reduced pressure. The crude product is subsequently fractionally distilled under reduced pressure. 305 g (55% of theory) of a light yellow liquid having a boiling point of 96° C. at 10 mbar are obtained.

The $^1$H NMR spectrum contained the following characteristic absorptions (CDCl$_3$, δ/ppm): 11.70 (s, 1H, OH); 6.41 (m, 1H, H-5); 3.71 (s, 2H, CH$_2$); 2.37 (s, 6H, N(CH$_3$)$_2$).

Example 7

Preparation of 2-hydroxy-4-(trifluoromethyl)-N,N-dimethylbenzylamine 195 g of 3-trifluoromethylphenol are initially charged in 160 ml of 40% aqueous dimethylamine solution and cooled to 15° C. At 155° C., 108 ml of 37% aqueous formaldehyde solution are added dropwise within 40 min. Subsequently, the mixture is stirred at room temperature for 20 hours. The mixture is cooled again to 15° C., admixed with 8 ml of 40% aqueous dimethylamine solution and 5.5 ml of 37% aqueous formaldehyde solution are added dropwise. Subsequently, the mixture is stirred at room temperature for a further 4.5 hours. The mixture is cooled again to 15° C. and admixed with 32 ml of 40% aqueous dimethylamine solution, and 21 ml of 37% aqueous formaldehyde solution are added dropwise. Subsequently, stirring is continued at room temperature for 17 hours. The mixture is admixed with 150 ml of water. The organic phase is removed, the aqueous phase is extracted twice with dichloromethane, the combined organic phases are washed once with water and the solvent is distilled off under reduced pressure. The crude product is taken up in 250 ml of water and adjusted to pH 1–2 with cooling in an ice bath using dilute hydrochloric acid. The acidic solution is extracted once with dichloromethane and subsequently adjusted to pH 11 with cooling in an ice bath using dilute sodium hydroxide solution. The alkaline reaction solution is extracted twice with dichloromethane, the combined organic phases are washed once with water and dried, and the solvent is distilled off under reduced pressure. The crude product is subsequently fractionally distilled under reduced pressure. 186 g (71% of theory) of a light yellow liquid having a boiling point of 91° C. at 14 mbar are obtained.

The $^1$H NMR spectrum contained the following characteristic absorptions (CDCl$_3$, δ/ppm): 7.08–6.98 (m, 3H, H-3, H-5, H-6); 3.67 (s, 2H, CH$_2$); 2.32 (s, 6H, N(CH$_3$)$_2$).

Example 8

Preparation of 4,5-difluoro-2-methylphenol 214 g of 4,5-difluoro-2-hydroxy-N,N-dimethylbenzylamine are initially charged in 700 ml of acetic acid in an autoclave, admixed with 50 g of palladium/activated carbon (5%) and heated with 70 bar of hydrogen to 100° C. for 26 hours. The autoclave is cooled and decompressed. The catalyst is filtered off and washed with acetic acid, and the filtrate is admixed with 3 000 ml of water. This aqueous solution is extracted three times with methyl tert-butyl ether. The combined organic phases are washed once with water and dried, and the solvent is distilled off under reduced pressure. The crude product is fractionally distilled under reduced pressure. The distillate can be further purified by crystallization. 98 g (58% of theory) of a colourless solid are obtained having a melting point of 68–70° C. and a boiling point of 78–80° C. at 13 mbar.

The $^1$H NMR spectrum contained the following characteristic absorptions (CDCl$_3$, δ/ppm): 6.92, 6.62 (2 m, 2H, H-3, H-6); 4.82 (s, 1H, OH); 2.19 (2, 3H, CH$_3$).

The following spectrum was obtained by means of GC-MS (EI, 70 eV, I/%): 144 (100, M$^+$); 126 (21, (M−F+H)$^+$).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing compounds of the formula (I)

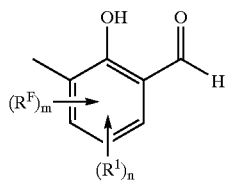

(I)

where

R$^1$ is in each case independently C$_1$–C$_{12}$-alkyl, chlorine or bromine or a radical of the formulae (IIa) or (IIb)

A-B-D-E (IIa)

A-E (IIb)

where, each independently,

A is absent or is a C$_1$–C$_8$-alkylene radical and

B is absent or is oxygen, sulphur or NR$^2$ where R$^2$ is hydrogen or C$_1$–C$_8$-alkyl and D is a carbonyl group and E is C$_1$–C$_8$-alkyl, C$_1$–C$_8$-alkoxy, NH(C$_1$–C$_8$-alkyl) or N(C$_1$–C$_8$-alkyl)$_2$ or is a cyclic amino radical having 4 to 12 carbon atoms and n is an integer of 0 to 3-m and R$^F$ is fluorine, C$_1$–C$_{12}$-fluoroalkyl, —O(C$_1$–C$_{12}$-fluoroalkyl) or —S(C$_1$–C$_{12}$-fluoroalkyl) and m is an integer of 1 to 3, comprising converting a compound of the formula (II)

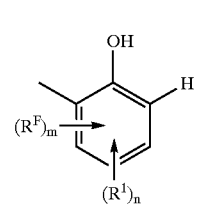

(II)

where R$^1$ and R$^F$, and also n and m, are as defined above in the presence of urotropin and in the presence of acid to compounds of the formula (I).

2. The process according to claim 1, wherein R$^1$ is in each case independently C$_1$–C$_4$-alkyl or chlorine.

3. The process according to claim 1, wherein n is 0 or 1.

4. The process according to claim 1, wherein R$^F$ is fluorine, C$_1$–C$_4$-fluoroalkyl, —O(C$_1$–C$_4$-fluoroalkyl) or —S(C$_1$–C$_4$-fluoroalkyl).

5. The process according to claim 1, wherein the molar ratio of urotropin to compounds of the formula (II) is 1:1 to 10:1.

6. The process according to claim 1, wherein the molar ratio of acid to compounds of the formula (II) is 1:1 to 100:1.

7. The process according to claim 1, wherein the acid used is one which, based on an aqueous reference system at 25° C., has a pK value of 3 or less.

8. The process according to claim 1, wherein the acids used are perfluoroalkylcarboxylic acids, ortho-phosphoric acid and polyphosphoric acids, organic sulphonic acids, hydrochloric, hydrobromic or hydriodic acid optionally dissolved in acetic acid, hydrogen sulphates or sulphuric acid.

9. The process according to claim 1, wherein the compounds of the formula (II) are prepared by converting compounds of the formula (III)

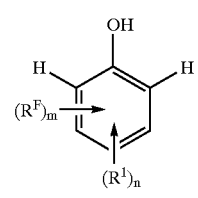

(III)

where

R$^1$, R$^F$ and m each have the definition specified above and n is an integer between 0 and 3-m, a) in the presence of formaldehyde and in the presence of secondary amines of the formula (IV)

HNR$^3$R$^4$ (IV)

where

R$^3$ and R$^4$ are each independently C$_1$–C$_8$-alkyl or NR$^3$R$^4$ as a whole is a cyclic amino radical having a total of 4 to 12 carbon atoms, into compounds of the formula (V)

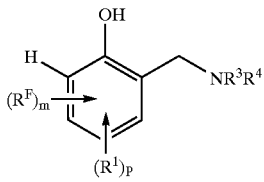

where
R$^1$, R$^3$, R$^4$ and R$^F$, and also n and m, each have the definition specified above, and
b) reducing the compounds of the formula (V) to compounds of the formula (II).

10. The process according to claim 9, wherein the molar ratio in step a) of formaldehyde to compounds of the formula (III) is 0.8 to 10.

11. The process according to claim 9, wherein the molar ratio in step a) of secondary amines of the formula (IV) to compounds of the formula (III) is 0.8 to 10.

12. The process according to claim 9, wherein the reduction of step b) is carried out in the presence of hydrogen and hydrogenation catalysts.

13. The process according to claim 12, wherein the hydrogenation catalyst used is a metal or metal compound selected from the group consisting of a salt or complex of nickel, palladium, platinum, cobalt, rhodium, iridium and ruthenium.

14. The process according to claim 12, wherein the reduction in step b) is effected at a reaction temperature of 20° C. to 200° C. and a partial hydrogen pressure of 0.1 to 180 bar.

15. A compound of the formula (I)

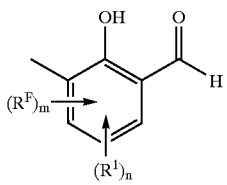

where
R$^1$ is in each case independently C$_1$–C$_{12}$-alkyl, chlorine or bromine or a radical of the formulae (IIa) or (IIb)

A-B-D-E (IIa)

A-E (IIb)

where, each independently,
A is absent or is a C$_1$–C$_8$-alkylene radical and
B is absent or is oxygen, sulphur or NR$^2$
where R$^2$ is hydrogen or C$_1$–C$_8$-alkyl and
D is a carbonyl group and
E is C$_1$–C$_8$-alkyl, C$_1$–C$_8$-alkoxy, NH(C$_1$–C$_8$-alkyl) or N(C$_1$–C$_8$-alkyl)$_2$ or is a cyclic amino radical having 4 to 12 carbon atoms and
n is an integer of 0 to 3-m and
R$^F$ is fluorine, C$_1$–C$_{12}$-fluoroalkyl, —O(C$_1$–C$_{12}$-fluoroalkyl) or —S(C$_1$–C$_{12}$-fluoroalkyl) and
m is an integer of 1 to 3.

16. The compound of formula (I) according to claim 15 selected from the group consisting of 5-fluoro-2-hydroxy-3-methylbenzaldehyde, 5,6-difluoro-2-hydroxy-3-methylbenzaldehyde and 2-hydroxy-3-methyl-5-(trifluoromethoxy)benzaldehyde.

17. A compound of the formula (II)

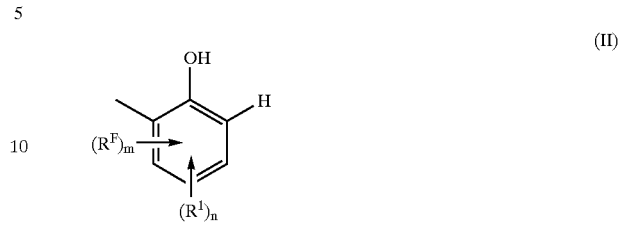

where
R$^1$ is in each case independently C$_1$–C$_{12}$-alkyl, chlorine or bromine or a radical of the formulae (IIa) or (IIb)

A-B-D-E (IIa)

A-E (IIb)

where, each independently,
A is absent or is a C$_1$–C$_8$-alkylene radical and
B is absent or is oxygen, sulphur or NR$^2$
where R$^2$ is hydrogen or C$_1$–C$_8$-alkyl and
D is a carbonyl group and
E is C$_1$–C$_8$-alkyl, C$_1$–C$_8$-alkoxy, NH(C$_1$–C$_8$-alkyl) or N(C$_1$–C$_8$-alkyl)$_2$ or is a cyclic amino radical having 4 to 12 carbon atoms and
n is an integer of 0 to 3-m and
R$^F$ is fluorine, C$_1$–C$_{12}$-fluoroalkyl, —O(C$_1$–C$_{12}$-fluoroalkyl) or —S(C$_1$–C$_{12}$-fluoroalkyl) and
m is an integer of 1 to 3,
with the exception of 4-fluoro-2-methylphenol.

18. The compound of formula (II) according to claim 17 selected from the group consisting of 4-fluoro-2-methylphenol, 4,5-difluoro-2-methylphenol and 2- methyl-4-(trifluoromethoxy)phenol.

19. A compounds of the formula (V)

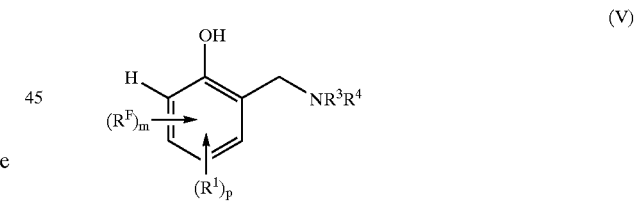

where
R$^1$ is in each case independently C$_1$–C$_{12}$-alkyl, chlorine or bromine or a radical of the formulae (IIa) or (IIb)

A-B-D-E (IIa)

A-E (IIb)

where, each independently,
A is absent or is a C$_1$–C$_8$-alkylene radical and
B is absent or is oxygen, sulphur or NR$^2$ where R$^2$ is hydrogen or C$_1$–C$_8$-alkyl and
D is a carbonyl group and
E is C$_1$–C$_8$-alkyl, C$_1$–C$_8$-alkoxy, NH(C$_1$–C$_8$-alkyl) or N(C$_1$–C$_8$-alkyl)$_2$ or is a cyclic amino radical having 4 to 12 carbon atoms and
n is an integer of 0 to 3-m and $R^F$ is fluorine, $C_1$–$C_{12}$-fluoroalkyl, —O($C_1$–$C_{12}$-fluoroalkyl) or —S($C_1$–$C_{12}$-fluoroalkyl) and m is an integer of 1 to 3 and $R^3$ and $R^4$ are each independently $C_1$–$C_8$-alkyl or $NR^3R^4$ as a whole is a cyclic amino radical having a total of 4 to 12 carbon atoms, with the exception of 5-fluoro-2-hydroxy-N,N-dimethylbenzylamine.

20. The compounds of formula (V) according to claim 19 selected from the group consisting of 4,5-difluoro-2-hydroxy-N,N-dimethyl-benzylamine, 2-hydroxy-5-(trifluoromethoxy)-N,N-dimethyl-benzylamine, 6-hydroxy-2,3,4-trifluoro-N, N-dimethylbenzylamine and 2-hydroxy-4-(trifluoromethyl)-N,N-dimethylbenzylamine.

21. A process for treating cardiovascular disorders and diseases comprising administering medicaments containing active ingredients based on compounds of claim 15 to subjects in need thereof.

* * * * *